(12) United States Patent
Price et al.

(10) Patent No.: US 7,517,497 B2
(45) Date of Patent: Apr. 14, 2009

(54) PASSIVE OSCILLATING DEVICE FOR CUTTING SAMPLE DISKS

(75) Inventors: Glenn Price, Martinez, CA (US); Hoa Nguyen, Pinole, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 554 days.

(21) Appl. No.: 11/397,832

(22) Filed: Apr. 3, 2006

(65) Prior Publication Data
US 2006/0245839 A1    Nov. 2, 2006

Related U.S. Application Data

(60) Provisional application No. 60/669,214, filed on Apr. 6, 2005.

(51) Int. Cl.
*B01L 3/00* (2006.01)
(52) U.S. Cl. .............. 422/99; 422/100; 83/24; 436/518; 204/606
(58) Field of Classification Search ........... 422/99–100; 83/24; 436/518; 204/606
See application file for complete search history.

(56) References Cited

U.S. PATENT DOCUMENTS

| | | | |
|---|---|---|---|
| 4,092,753 A | 6/1978 | Fuhrmann | |
| 4,809,553 A | 3/1989 | Reed, III | |
| 5,024,565 A | 6/1991 | Pinand | |
| 5,125,131 A | 6/1992 | Leblanc | |
| 5,937,534 A | 8/1999 | Anderson et al. | |
| 6,342,143 B1 | 1/2002 | Minden | |
| 6,526,812 B2 | 3/2003 | Martin et al. | |

FOREIGN PATENT DOCUMENTS

| WO | WO 99/15875 A1 | 4/1999 |
|---|---|---|
| WO | WO 00/57153 A1 | 9/2000 |

OTHER PUBLICATIONS

Houck, David R.; "Automated Processing of 2-D Protein Gels"; 2003, *Genetic Engineering* News, vol. 23, No. 2, pp. 28-30.

*Primary Examiner*—Jill Warden
*Assistant Examiner*—Jyoti Nagpaul
(74) *Attorney, Agent, or Firm*—Townsend and Townsend and Crew LLP.; M. Henry Heines

(57) ABSTRACT

Sample disks are excised from a membrane by a cutting apparatus that includes a cutting tool terminating in a hollow cylinder with an exposed cutting edge, the tool slidably retained within a sleeve or otherwise slidably mounted to a mounting body, with a spiral cam in either the tool or the mounting body. A rider is included in the construction and arranged to engage the cam such that sliding movement of the cutting tool translates into rotational movement of the cylinder and its cutting edge.

8 Claims, 2 Drawing Sheets

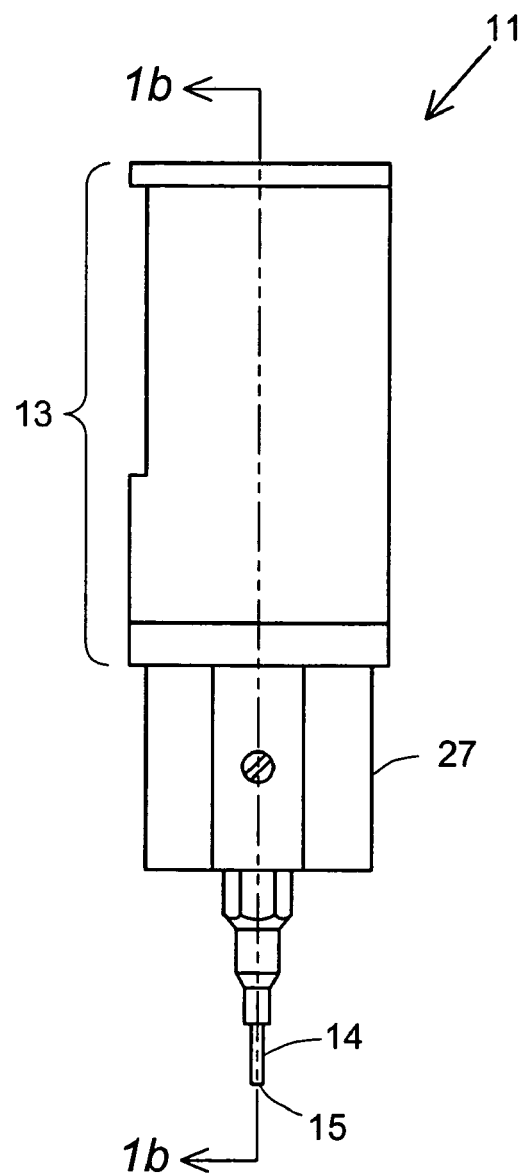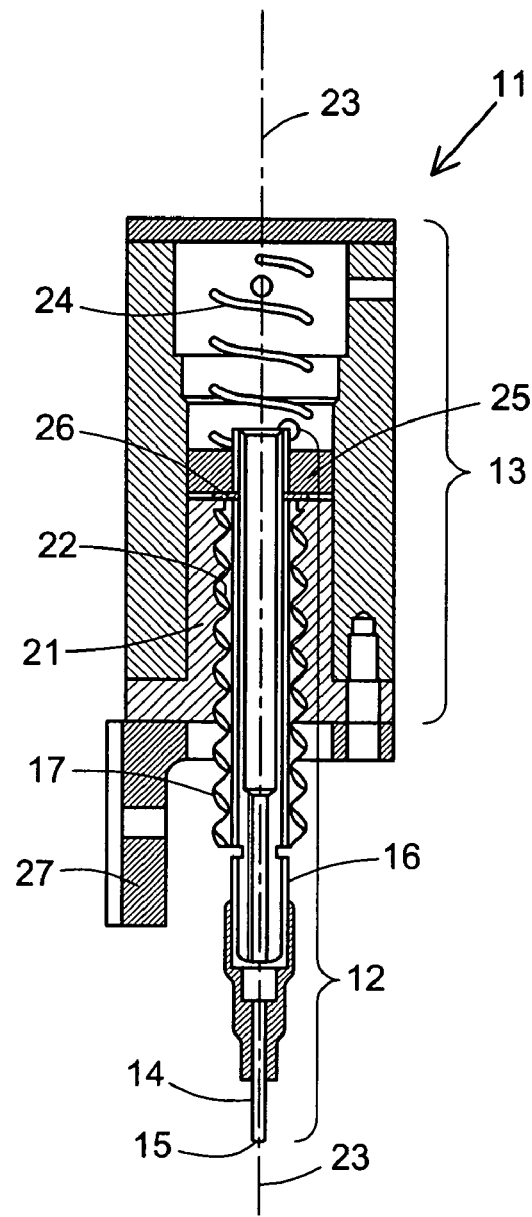
Fig. 1a
Fig. 1b

PASSIVE OSCILLATING DEVICE FOR CUTTING SAMPLE DISKS

CROSS-REFERENCE TO RELATED APPLICATION

This application claims benefit from U.S. Provisional Patent Application No. 60/669,214, filed Apr. 6, 2005, the contents of which are incorporated herein by reference in their entirety.

BACKGROUND OF THE INVENTION

1. Field of the Invention

This invention resides in the field of biochemical laboratory equipment, and particularly equipment that is used for analyses of multitudes of small samples of biologically derived mixtures.

2. Description of the Prior Art

Many biochemical laboratories perform procedures that involve analyses of large numbers of samples, each containing biological species that are very similar in structure and each available only in very small quantities. Analysis of this kind are performed in a sequence of stages, each stage requiring close control of the reaction conditions while maintaining individual handling of each sample. To accomplish this, the samples are often arranged in two-dimensional arrays, and sophisticated instrumentation, frequently involving robotics, is used to remove individual samples from an array and transport the samples to various stations where the different stages of the procedure are performed. Proteomics is an example of such a procedure. The species to be isolated in proteomics typically reside in spots on a two-dimensional gel or on a membrane to which the spots have been transferred from a gel. Polyvinylidene difluoride (PVDF) and nitrocellulose are examples of materials from which such membranes are made. The individual stages in a proteomics procedure include imaging of the array and location of the spots, plus excision of the spots from the array, transfer of the excised spots to various locations, digestion of the substances contained in the spots, and analysis of the digested substances, all performed by the instrument under computer control. The digestion and analysis steps are typically performed in the wells of a multi-well plate such as a 96-well microplate, and excision of the spots from the membrane and transfer to the wells are performed by an automated spot cutter which is controlled by the robotics. A typical spot cutter is a hollow cylinder that is approximately the size of a hypodermic needle. The cylinder is movable in the x-y plane for positioning over individual spots, and in the z-direction to be lowered onto the gel or membrane to cut a very small disk containing the spot from the gel or membrane. Disclosures of robotics-containing instrumentation for performing this task are found in International Patent Publication No. WO 99/15875, MacQuarie Research Ltd., applicant, publication date 1 Apr. 1999 ("Apparatus for Removing a Sample From an Array of Samples and a Cutting Tool for Use With That Apparatus"); and International Patent Publication No. WO 00/57153, Campbell Corporation Pty. Ltd., applicant, publication date 28 Sep. 2000 ("Improvements in Apparatus and Method for Removing Samples"). An example of instrumentation that incorporates disk-excising robotics is the 2DiD integrated system for imaging and spot-picking of LEAP Technologies (Carrboro, N.C., USA). When the disk is to be cut from a membrane support material such as PVDF or nitrocellulose, the cylinder in certain instruments is rotated during the cutting operation to facilitate the cutting of the membrane by the cylinder edge. The above-referenced Publication No. WO 00/57153 discloses a "belt and pulley arrangement" for accomplishing this rotation.

SUMMARY OF THE INVENTION

The present invention resides in a disk cutting apparatus whose cutting element is a rotating hollow cylinder the rotation of which is driven by the vertical movement of the apparatus. The mechanism is similar in principle to what is traditionally known as a "Yankee" or "Yankee-style" screwdriver, i.e., two parts slidably mounted to each other with a spiral race on one part and a rider on the other such that linear motion of the parts relative to each other is converted to rotational motion of one of the parts. In the present invention, one of the two parts is the hollow cylinder or a shaft to which the hollow cylinder is mounted, and the other is a body that is mountable to the instrument, preferably a robotics-containing instrument, that controls the position, including the vertical movement, of the mounting body. The hollow cylinder, or the combination of the hollow cylinder and a shaft when the cylinder is mounted to a shaft, is referred to herein as a "cutting tool." In preferred embodiments, the mounting body is a sleeve or housing that receives one end of the cutting tool and allows the cutting tool to at least partially retract inside the sleeve, achieving rotation of the cutting tool by sliding the sleeve over the cutting tool. The disk cutting operation is thereby achieved by simply contacting the membrane with the exposed cutting edge of the hollow cylinder and pressing the entire device further against the membrane to force the sleeve or mounting body over the hollow cylinder. This causes the cylinder to rotate so that its cutting edge will cut a disk cleanly and uniformly from the membrane.

These and other features, embodiments, objects, and advantages of the invention will be apparent from the description that follows.

BRIEF DESCRIPTION OF THE DRAWINGS

FIG. 1a is a side view of a cutting apparatus in accordance with the present invention, and FIG. 1b is a cross section of the same apparatus taken along the line 1b-1b of FIG. 1a. FIGS. 1a and 1b show the apparatus in a relaxed configuration.

FIGS. 2a and 2b are side and cross section views of the same cutting apparatus shown in FIGS. 1a and 1b but with the apparatus in a compressed configuration. The cross section of FIG. 2b is taken along the line 2b-2b of FIG. 2a.

DETAILED DESCRIPTION OF THE INVENTION AND PREFERRED EMBODIMENTS

Figure 2A:
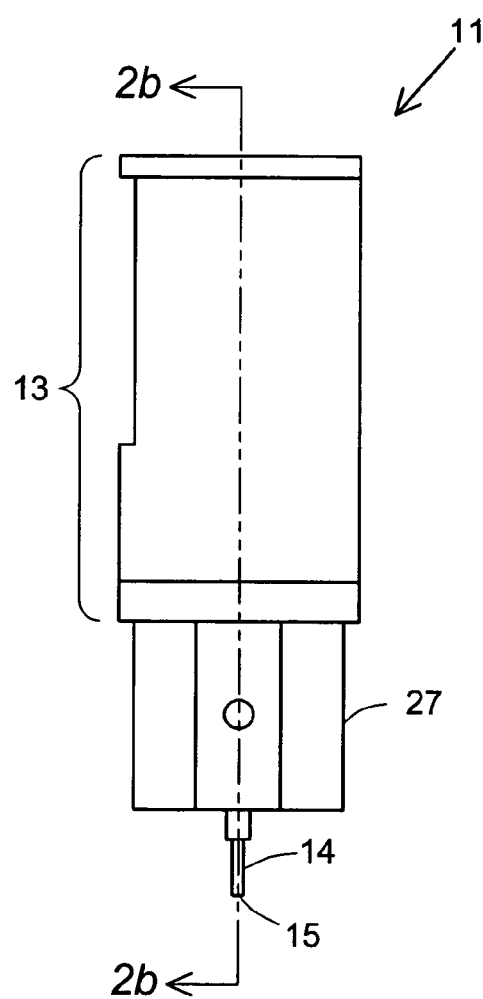

As noted above, one of the ways in which the present invention differs from the "Yankee-style" screwdriver is by the inclusion of the hollow cylinder as the rotating component in the invention rather than a screwdriver blade, and by the cutting function of the cylinder. In certain embodiments, the present invention may adopt the "Yankee-style" rotational options by containing two superimposed spiral cams that spiral in opposite directions, i.e., one clockwise and the other counter-clockwise, and a variable rider that can be adjusted to follow one cam to the exclusion of the other, thereby offering to the user, or to the automated instrument, a choice of rotational direction. In other, preferred embodiments, a single spiral cam is included so that rotation occurs in only one direction as the cutting tool is retracted and in the opposite direction as the cutting tool is extended. The cutting function is preferably performed during retraction of the cutting tool as the entire device is pressed against the membrane. The direction of rotation during retraction is not critical and can be either clockwise or counter-clockwise.

The cutting tool is biased relative to the mounting body so that pressing the device against the membrane will necessarily cause the cutting tool to slide relative to the mounting body and thereby rotate. When the mounting body is a sleeve, the cutting tool is biased in an extended position so that pressure against the membrane will cause retraction of the tool. The biasing can be achieved by gravitational force when the device is held or mounted with the axis of the cutting tool in a vertical orientation and the cylinder depending downward from the body. Alternatively, and preferably, the biasing is achieved by spring-loading, either with a conventional coil spring or any known equivalent of a coil spring.

The term "cam" is used herein to denote any rotating or sliding component in a mechanical linkage that transforms linear motion into rotary motion. A preferred cam in the present invention is a spiral race, which term denotes a groove cut into the surface of either the cutting tool or the mounting body and forming a spiral in the direction of motion. The term "rider" is used herein to denote a component that engages the spiral race by following the race as one of the two components moves relative to the other. The rider can therefore for example be either a simple projection, a ball retained in a recess, or a spiral ridge complementary to the spiral race. The spiral race can reside either on the cutting tool or on the mounting body, although is preferably on the cutting tool. Alternatively, particularly when the mounting body is a sleeve, the spiral race and rider can be identical in configuration, i.e., two matching threaded surfaces, one on the outer surface of the cutting tool and the other on the inner surface of the sleeve.

To attach the cutting apparatus of this invention to an instrument that performs the functions enumerated in the "Background of the Invention" above, the apparatus contains a mounting bracket whose structure and means of attachment are not critical. The bracket will enable the instrument to manipulate the device, including the vertical movement that produces the cutting action. The instrument will preferably also provide translational movement in the horizontal direction, so that the device can be positioned over any portion of the membrane.

In view of these various possibilities, the present invention is susceptible to a wide range of variation. A detailed review of one particular embodiment however will provide an understanding of the function and operation of the invention in each of its embodiments. The figures hereto depict one such embodiment.

Figure 2B:
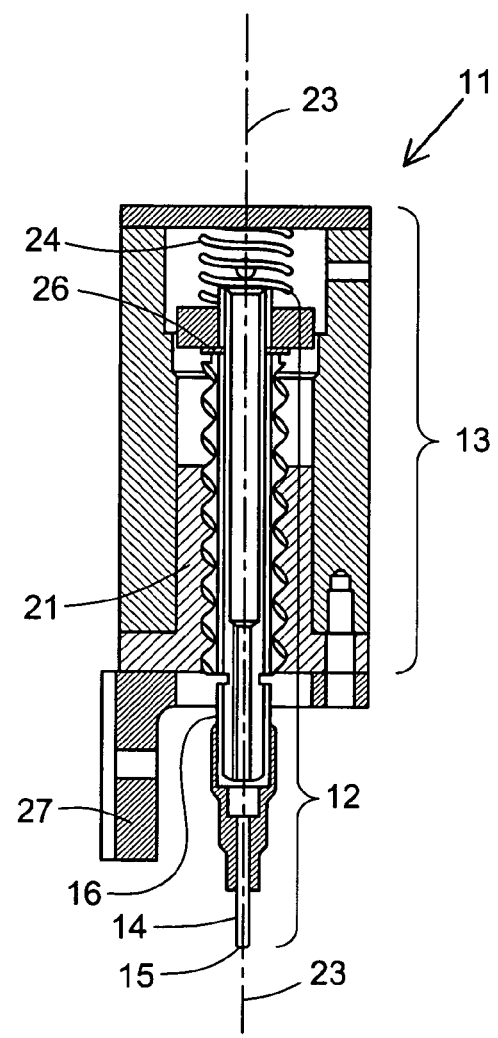

FIGS. 1a and 1b are side and cross-section views of a cutting apparatus 11 in accordance with this invention, whose component parts include a cutting tool 12 and a mounting body in the form of a housing 13. The apparatus is shown in the relaxed configuration in FIGS. 1a and 1b with the cutting tool 12 fully extended. FIGS. 2a and 2b are side and cross-section views of the same cutting apparatus 11 but in the compressed configuration with the cutting tool 12 partially retracted inside the housing 13. The cross section of FIG. 1b is taken along the line 1b-1b of FIG. 1a, and likewise the cross section of FIG. 2b is taken along the line 2b-2b of FIG. 2a.

The cutting tool 12 includes a hollow cylinder 14 that terminates with an exposed cutting edge 15. In operation, this cutting edge 15 penetrates the membrane (not shown) and cuts the spot in the shape of a small disk (not shown) from the membrane. Thus cut, the disk is retained in the interior of the hollow cylinder 14 during transport of the disk to a reaction well or other location where the next stage of the procedure is to be performed. Once transported, the disk can expelled from the cylinder by conventional means, which can include hydraulic pressure, a partial vacuum, or an internal rod. The cylinder is mounted to a support shaft 16 whose exterior is shaped to form a spiral race which in this embodiment is a thread 17 allowing the shaft to function as a lead screw. The housing 13 includes as part of its structure an insert 21 whose internal surface is contoured to form the rider, which in this embodiment is also a thread 22 that is complementary to the thread 17 on the external surface of the shaft 16 of the cutting tool. The insert 21 thus serves as a lead screw nut operating in conjunction with the lead screw of the shaft 16. The interaction of the shaft 16 and the housing insert 21 translates the up and down motion of the shaft along the cylinder axis 23 (i.e., inward and outward relative to the housing) into a rotary motion in the form of a counter-clockwise rotation as the shaft 16 as the shaft is forced into the housing 13 and a clockwise rotation as the shaft is released.

A coil spring 24 inside the housing 13 controls the position of the cutting tool 15 relative to the housing, thereby providing the biasing function referred to above. During the cutting action, when the cutting edge 15 is pressed against the sheet from which the spot is to be cut, the cutting tool 12 compresses the spring 23, as shown in FIG. 2b. Release of the spring 24 returns the cutting tool to the position shown in FIGS. 1a and 1b. A thrust bearing 25 supports the spring while the thrust bearing itself rests on a retaining ring 26 that is held in a groove encircling the exterior surface of the cutting tool shaft 16. The thrust bearing 25 rotates with the lead screw; the spring 24 however does not rotate. The thrust bearing 25 preferably contains actual bearings that will reduce or eliminate any friction between the shaft 16, retaining ring 26, and bearing 25 (all of which rotate) and the non-rotating spring 24. A mounting bracket 27 secures the housing to moving parts of a robotics-controlled instrument (not shown) which allows the housing to be moved in the x, y, and z directions, the z direction being the direction in which the cutting tool 12 moves relative to the housing 13 to produce the rotary cutting motion.

The foregoing is offered primarily for purposes of illustration. Variations in the shapes and arrangements of the various components that still incorporate the basic elements of this invention, as expressed in the appended claims, will be readily apparent to those skilled in the art of laboratory equipment and its design, construction, and use.

In the appended claims, the terms "comprise," "comprises," and "comprising" all denote the inclusion of the element, component, or step, or group of elements, components, or steps, that follow the term, but not the exclusion of any other element, component or step not expressly stated. Likewise, the terms "a" and "an" denote "one or more."

What is claimed is:

1. Apparatus for cutting a disk from a membrane, said apparatus comprising:

a cutting tool comprising a hollow cylinder having a cylinder axis, said hollow cylinder terminating in a cutting edge, and said cutting tool slidably secured to a mounting body;

a spiral cam on one of said cutting tool and said mounting body, and a rider on the other of said cutting tool and said mounting body, said rider engaging said spiral cam whereby linear motion of said cutting tool relative to said mounting body is converted to rotational motion of said hollow cylinder about said cylinder axis;

biasing means for urging said cutting tool in one direction relative to said mounting body; and means for mounting said mounting body to an instrument that moves said mounting body in a direction parallel to said cylinder axis.

2. The apparatus of claim 1 wherein said cutting tool further comprises a shaft affixed to and coaxial with said hollow cylinder, and said spiral cam is on said shaft.

3. The apparatus of claim 2 wherein said hollow cylinder is mounted to a first end of said shaft and said mounting body is a housing receiving a second end of said shaft, and said biasing means urges said shaft outward from said housing.

4. The apparatus of claim 3 wherein said biasing means comprises spring means disposed within said housing.

5. The apparatus of claim 1 wherein said spiral cam is a spiral race.

6. The apparatus of claim 5 wherein said rider is a spiral ridge complementary in contour to said spiral race.

7. The apparatus of claim 5 wherein said spiral race is in said mounting body surface.

8. The apparatus of claim 1 wherein said means for mounting said mounting body to said instrument comprises a bracket projecting from said housing.

* * * * *